United States Patent
Inoue et al.

(10) Patent No.: US 11,672,743 B2
(45) Date of Patent: Jun. 13, 2023

(54) COMPOSITION FOR KERATIN FIBERS COMPRISING A DIRECT DYE

(71) Applicant: L'OREAL, Paris (FR)

(72) Inventors: Ayu Inoue, Kawasaki (JP); Hayato Nishimura, Kamakura (JP); Kazumitsu Kawakami, Westfield, NJ (US); Celine Bossard, Kawasaki (JP); Dhimoy Roy, Kawasaki (JP)

(73) Assignee: L'OREAL, Paris (FR)

( * ) Notice: Subject to any disclaimer, the term of this patent is extended or adjusted under 35 U.S.C. 154(b) by 26 days.

(21) Appl. No.: 17/296,435

(22) PCT Filed: Nov. 5, 2019

(86) PCT No.: PCT/JP2019/044038
§ 371 (c)(1),
(2) Date: May 24, 2021

(87) PCT Pub. No.: WO2020/110675
PCT Pub. Date: Jun. 4, 2020

(65) Prior Publication Data
US 2022/0015997 A1    Jan. 20, 2022

(30) Foreign Application Priority Data

Nov. 27, 2018 (JP) .............................. JP2018-221081

(51) Int. Cl.
| | |
|---|---|
| *A61Q 5/10* | (2006.01) |
| *A61K 8/06* | (2006.01) |
| *A61K 8/34* | (2006.01) |
| *A61K 8/891* | (2006.01) |
| *A61K 8/92* | (2006.01) |
| *A61Q 5/06* | (2006.01) |

(52) U.S. Cl.
CPC .............. *A61K 8/064* (2013.01); *A61K 8/345* (2013.01); *A61K 8/891* (2013.01); *A61K 8/92* (2013.01); *A61Q 5/065* (2013.01); *A61K 2800/432* (2013.01)

(58) Field of Classification Search
CPC ........ A61K 8/064; A61K 8/345; A61K 8/891; A61K 8/92; A61K 2800/432; A61K 8/31; A61K 8/8147; A61Q 5/065; A61Q 5/12
USPC ............................................................. 8/405
See application file for complete search history.

(56) References Cited

U.S. PATENT DOCUMENTS

| | | | | |
|---|---|---|---|---|
| 2008/0184496 | A1* | 8/2008 | Brun | ...................... A61K 8/893 8/405 |
| 2017/0326041 | A1* | 11/2017 | Tsuzuki | ................. A61K 8/345 |

FOREIGN PATENT DOCUMENTS

| | | |
|---|---|---|
| CN | 105209123 A | 12/2015 |
| EP | 2065030 A1 | 6/2009 |
| EP | 2156819 A1 | 2/2010 |
| JP | 2008-056621 A | 3/2008 |
| JP | 2008-546807 A | 12/2008 |
| JP | 2009-132625 A | 6/2009 |
| JP | 2014-501773 A | 1/2014 |
| JP | 2018-052841 A | 4/2018 |
| WO | 2007/002566 A2 | 1/2007 |
| WO | 2016/08497 A1 | 6/2016 |
| WO | 2016/084971 A1 | 6/2016 |
| WO | 2018/221257 A1 | 12/2018 |

OTHER PUBLICATIONS

International Search Report for counterpart Application No. PCT/JP2019/044038, dated Mar. 12, 2020.
Mintel: "Semi-Permanent Hair Color," Hoyu America, XP055662356, retrieved from www.gnpd.com, Database accession No. 6097701, Nov. 5, 2018.
Translation of Japanese Office Action for Application No. JP 2018-221081, dated Aug. 1, 2022.
Mintel: "Semi-Permanent Hair Color," Hoyu America, XP055663256, retrieved from www.gnpd.com, Database accession No. 6097701, Nov. 5, 2018.
Translation of Chinese Office Action for Application No. 201980077505. 9, dated Oct. 20, 2022.
English Translation of Korean Notice of Grounds for Rejection of Application No. 10-2021-7015617, dated Mar. 2, 2023.

* cited by examiner

*Primary Examiner* — Eisa B Elhilo
(74) *Attorney, Agent, or Firm* — The Marbury Law Group, PLLC

(57) ABSTRACT

The present invention relates to a composition for treating keratin fibers, preferably hair, comprising: (a) at least one direct dye; (b) at least one oil; (c) at least one polyol; and (d) water, wherein the amount of the (a) direct dye(s) in the composition is 0.01% by weight or more relative to the total weight of the composition, and the amount of the (b) oil(s) in the composition is 20% by weight or more, preferably 30% by weight or more, and more preferably 40% by weight or more, relative to the total weight of the composition, provided that the (b) oil comprises at least one silicone oil. The composition according to the present invention is stable and can be used for coloring keratin fibers, in particular for the maintenance of the color of the keratin fibers, while providing the keratin fibers with smoothness and alignment.

19 Claims, No Drawings

COMPOSITION FOR KERATIN FIBERS COMPRISING A DIRECT DYE

CROSS REFERENCE TO RELATED APPLICATION

This is a national stage application of PCT/JP2019/044038, filed internationally on Nov. 5, 2019, which claims priority to Japanese Application No. 2018-221081, filed on Nov. 27, 2018, both of which are incorporated by reference herein in their entireties.

TECHNICAL FIELD

The present invention relates to a composition for treating keratin fibers, preferably hair.

BACKGROUND ART

In the field of hair cosmetic treatments, leave-on type and rinse-off type hair cosmetics yare important sectors in the hair care category, and consumers use these hair cosmetics to provide hair with smoothness and the like.

JP-A-2009-132625 discloses a transparent hair cosmetic composition including a specific cationic surfactant, an ethyleneoxide adduct of 1,2-dodecanediol, and water, wherein the amounts of these ingredients are limited to certain ranges.

JP-T-2008-546807 also discloses a transparent or translucent hair cosmetic composition including a thickener, a cationic surfactant and/or a nonionic surfactant, and a hydrophobicized amidosilicone copolyol, wherein the amounts of these ingredients are limited to certain ranges.

However, they are not intended for coloring hair in particular for the maintenance of hair color while providing hair with smoothness and alignment. In addition, a composition for treating keratin fibers should be stable without causing phase separations.

DISCLOSURE OF INVENTION

An objective of the present invention is to provide a composition for keratin fibers such as hair, which is stable and can color the keratin fibers, in particular for the maintenance of the color of the keratin fibers, while providing the keratin fibers with smoothness and alignment.

The above objective can be achieved by a composition for treating keratin fibers, preferably hair, comprising:
(a) at least one direct dye;
(b) at least one oil;
(c) at least one polyol; and
(d) water,
wherein
the amount of the (a) direct dye(s) in the composition is 0.01% by weight or more relative to the total weight of the composition, and
the amount of the (b) oil(s) in the composition is 20% by weight or more, preferably 30% by weight or more, and more preferably 40% by weight or more, relative to the total weight of the composition,
provided that the (b) oil comprises at least one silicone oil.

The amount of the (b) oil(s) in the composition according to the present invention may be 80% by weight or less, preferably 70% by weight or less, and more preferably 60% by weight or less, relative to the total weight of the composition.

The silicone oil may comprise either at least one volatile silicone oil or at least one non-volatile silicone oil, or both of at least one volatile silicone oil and at least one non-volatile silicone oil. The volatile silicone oil may be selected from cyclic silicones. The non-volatile silicone oil may be selected from polydimethylsiloxanes and organo-modified polydimethylsiloxanes. The organo-modified polydimethylsiloxane may be selected from dimethicone copolyols. The amount of the silicone oil(s) in the composition according to the present invention may range from 1% to 25% by weight, preferably from 3% to 20% by weight, and more preferably from 5% to 15% by weight, relative to the total weight of the composition.

The (c) polyol may be selected from the group consisting of glycerin, ethyleneglycol, polyethyleneglycol, propyleneglycol, dipropyleneglycol, butyleneglycol, pentyleneglycol, hexyleneglycol and mixtures thereof The amount of the (c) polyol(s) in the composition according to the present invention may range from 1% to 30% by weight, preferably from 5% to 25%, and more preferably from 10% to 20%, relative to the total weight of the composition.

The amount of the (d) water in the composition according to the present invention may range from 1% to 40% by weight, preferably from 5% to 35% by weight, and more preferably from 10% to 30% by weight, relative to the total weight of the composition.

The weight ratio of the amount of the (d) water/the amount of the (c) polyol(s) may be 3 or less, preferably 2 or less, and more preferably 1 or less. The weight ratio of the amount of the (d) water/the amount of the (c) polyol(s) may be 0.1 or more, more preferably 0.2 or more, and more preferably 0.3 or more.

The composition according to the present invention may further comprise (e) at least one hydrophilic acrylic polymer.

The composition according to the present invention may be a leave-on type or rinse-off type.

The present invention also relates to a cosmetic process for keratin fibers, preferably hair, comprising the step of applying the composition according to the present invention to the keratin fibers.

BEST MODE FOR CARRYING OUT THE INVENTION

After diligent research, the inventors have discovered that it is possible to provide a composition for keratin fibers such as hair, which is stable and can color the keratin fibers, in particular for the maintenance of the color of the keratin fibers, while providing the keratin fibers with smoothness and alignment.

Thus, the present invention mainly relates to a composition for treating keratin fibers, preferably hair, comprising:
(a) at least one direct dye;
(b) at least one oil;
(c) at least one polyol; and
(d) water,
wherein
the amount of the (a) direct dye(s) in the composition is 0.01% by weight or more relative to the total weight of the composition, and
the amount of the (b) oil(s) in the composition is 20% by weight or more, preferably 30% by weight or more, and more preferably 40% by weight or more, relative to the total weight of the composition,
provided that the (b) oil comprises at least one silicone oil.

The composition according to the present invention includes at least one direct dye. Therefore, the composition according to the present invention can color keratin fibers.

The composition according to the present invention can be used for coloring keratin fibers, in particular for the maintenance of the color of the keratin fibers, while providing the keratin fibers with smoothness and alignment.

The term "maintenance of the color of keratin fibers" means providing keratin fibers with a color which may be the same as or different from the color of the keratin fibers. The color of the keratin fibers may be the original color of the keratin fibers or the artificial or dyed color which has already been provided to the keratin fibers by dyeing the keratin fibers.

If a color which is the same as the color of the keratin fibers is provided by the present invention, the color of the keratin fibers appears maintained as being fresh. Therefore, for example, the fading over time of the dyed color of the keratin fibers can be concealed. On the other hand, if a color which is different from the color of the keratin fibers is provided by the present invention, the color of the keratin fibers can be easily changed or modified. For example, if a complementary color is provided by the present invention, a combination of the provided color and the color of the keratin fibers can result in the decrease of the chroma of the color of the keratin fibers, and therefore, the fading over time of, for example, the dyed color of the keratin fibers can be less noticeable.

The term "smoothness" means that the surface friction on the keratin fibers is reduced. Therefore, the present invention can make (for example) the following possible: smooth combing, smooth feeling to touch when the keratin fibers are dry, and ease of running fingers through the keratin fibers even if the keratin fibers are wet.

The term "alignment" means that the keratin fibers become less unruly. Therefore, the scope of "alignment" includes volume reduction of the keratin fibers, e.g., the spreading of the keratin fibers is reduced or controlled, and therefore, the styling of the keratin fibers can be well controlled.

The composition according to the present invention can also provide keratin fibers such as hair with additional improved conditioning and manageability cosmetic effects such as anti-frizz effects.

The composition according to the present invention includes at least one silicone oil. In general, the presence of silicone may cause instability issues. However, the composition according to the present invention is stable.

The composition according to the present invention may be transparent and the transparent aspect of the present invention is stable over time; therefore, the composition according to the present invention can be attractive to consumers.

Hereafter, the present invention will be described in a detailed manner.

[Composition]

One aspect of the present invention relates to a composition for treating keratin fibers, preferably hair, comprising:
(a) at least one direct dye;
(b) at least one oil;
(c) at least one polyol; and
(d) water,
wherein
the amount of the (a) direct dye(s) in the composition is 0.01% by weight or more relative to the total weight of the composition, and
the amount of the (b) oil(s) in the composition is 20% by weight or more, preferably 30% by weight or more, and more preferably 40% by weight or more, relative to the total weight of the composition,
provided that the (b) oil comprises at least one silicone oil.

{Direct Dye}

The composition according to the present invention includes at least one direct dye. Two or more direct dyes may be used in combination. Thus, a single type of direct dye or a combination of different types of direct dyes may be used.

A direct dye means a colored substance which does not require the use of an oxidizing agent in order to develop its color.

The direct dye may be a natural direct dye or a synthetic direct dye.

The expression "natural direct dye" is understood to mean any dye or dye precursor that is naturally occurring and is produced by extraction (and optionally purification) from a plant matrix or an animal such as an insect, optionally in the presence of natural compounds such as ash or ammonia.

As natural direct dyes, mention may be made of quinone dyes (such as lawsone and juglone), alizarin, purpurin, laccaic acid, carminic acid, kermesic acid, purpurogallin, protocatechaldehyde, indigoids such as indigo, sorghum, isatin, betanin, curcuminoids (such as curcumin), spinulosin, various types of chlorophyll and chlorophyllin, hematoxylin, hematein, brazilein, brazilin, safflower dyes (such as carthamin), flavonoids (such as rutin, quercetin, catechin, epicatechin, morin, apigenidin, and sandalwood), anthocyans (such as apigeninidin and apigenin), carotenoids, tannins, orceins, santalins and cochineal carmine.

It is also possible to use extracts or decoctions containing natural direct dye(s), in particular henna-based extracts, *Curcuma longa* extract, sorghum leaf-sheath extract, haematoxylon campechianum extract, green tea extract, pine bark extract, cocoa extract, and logwood extract.

It is preferable that the natural direct dye be chosen from the group consisting of curcuminoids, santalins, chlorophyllin, haematoxylin, haematein, brazilein, brazilin, sorghum, laccaic acid, lawsone, juglone, alizarin, purpurin, carminic acid, kermesic acid, purpurogallin, protocatechaldehyde, indigoids, isatin, spinulosin, apigenin, orcein, betanin, flavonoids, anthocyans, and extracts or decoctions containing these compounds.

Alternatively, the natural direct dyes may be preferably chosen, for example, from hydroxylated quinones, indigoids, hydroxyflavones, santalins A and B, isatin and its derivatives, and brasilin and its hydroxylated derivative.

The hydroxylated quinones are preferably benzoquinones, naphthoquinones, and mono- or polyhydroxylated anthraquinones which are optionally substituted with groups such as alkyl, alkoxy, alkenyl, chloro, phenyl, hydroxyalkyl and carboxyl.

The naphthoquinones are preferably lawsone, juglone, flaviolin, naphthazarin, naphthopurpurin, lapachol, plumbagin, chloroplumbagin, droserone, shikonin, 2-hydroxy-3-methyl-1,4-naphthoquinone, 3,5-dihydroxy-1,4-naphthoquinone, 2,5-dihydroxy-1,4-naphthoquinone, 2-methoxy-5-hydroxy-1,4-naphthoquinone and 3-methoxy-5-hydroxy-1,4-naphthoquinone.

The benzoquinones are preferably spinulosin, atromentin, aurentioglyocladin, 2,5-dihydroxy-6-methylbenzoquinone, 2-hydroxy-3-methyl-6-methoxybenzoquinone, 2, 5-dihydroxy-3,6-diphenylbenzoquinone, 2,3-dimethyl-5-hydroxy-6-methoxybenzoquinone and 2,5-dihydroxy-6-isopropylbenzoquinone.

The anthraquinones are preferably alizarin, quinizarin, purpurin, carminic acid, chrysophanol, kermesic acid, rhein, aloe emodin, pseudopurpurin, quinizarincarboxylic acid, frangula emodin, 2-methylquinizarin, 1-hydroxyanthraquinone and 2-hydroxyanthraquinone.

The indigoids are preferably indigo, indirubin, isoindigo and Tyrian purple.

The hydroxyflavones are preferably quercetin and morin.

The expression "synthetic direct dye" is understood to mean any dye or dye precursor that is produced by chemical synthesis.

The direct dye can be selected from the group consisting of acidic (anionic) direct dyes, basic (cationic) direct dyes, and neutral (nonionic) direct dyes.

Non-limiting examples of synthetic dyes include (non-ionic) neutral, anionic (acidic), and cationic (basic) dyes such as azo, methine, carbonyl, azine, nitro(hetero)aryl types or tri(hetero)arylmethane direct dyes, porphyrins and phthalocyanines, alone or as mixtures.

More particularly, the azo dyes comprise an —N=N— functional group, the two nitrogen atoms of which are not simultaneously involved in a ring. However, it is not ruled out for one of the two nitrogen atoms of the —N=N— sequence to be involved in a ring.

The dyes of the family of the methines are more particularly compounds comprising at least one sequence chosen from >C=C< and —N=C<, the two atoms of which are not simultaneously involved in a ring. However, it is specified that one of the nitrogen or carbon atoms of the sequences can be involved in a ring. More particularly, the dyes of this family result from compounds of the following types: true methine (comprising one or more of the above-mentioned —C=C— sequences); azomethine (comprising at least one or more —C=N— sequences) with, for example, the azacarbocyanines and their isomers, the diazacarbocyanines and their isomers, the tetraazacarbocyanines; mono- and diaryl-methane; indoamines (or diphenylamines); indophenols; indoanilines.

As the dyes of the family of the carbonyls, mention may be made, for example, of synthetic dyes chosen from acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, naphthalimide, anthra-pyrimidine, diketopyrrolopyrrole or coumarin dyes.

As the dyes of the family of the cyclic azines, mention may be made, in particular, of azine, xanthene, thioxanthene, fluorindine, acridine, (di)oxazine, (di)thiazine or pyronine dyes.

The nitro(hetero)aromatic dyes are more particularly nitrobenzene or nitropyridine direct dyes.

As the dyes of porphyrin or phthalocyanine type, use may be made of cationic or noncationic compounds optionally comprising one or more metals or metal ions, such as, for example, alkali and alkaline earth metals, zinc and silicon.

Mention may be made, as examples of synthetic direct dyes which are particularly suitable, of nitrobenzene dyes, azo, azomethine or methine direct dyes, azacarbocyanines, such as tetraazacarbocyanines (tetraazapentamethines), quinone and in particular anthraquinone, naphthoquinone or benzoquinone direct dyes, or azine, xanthene, triarylmethane, indoamine, phthalocyanine and porphyrin direct dyes, alone or as mixtures. More preferably still, these synthetic direct dyes are chosen from nitrobenzene dyes, azo, azomethine or methine direct dyes and tetraazacarbocyanines (tetraazapentamethines); alone or as mixtures.

Mention may be made, among the azo, azomethine, methine or tetraazapentamethine direct dyes which can be used according to the present invention, of the cationic dyes described in Patent Applications WO 95/15144, WO 95/01772 and EP 714 954; FR 2 189 006, FR 2 285 851, FR-2 140 205, EP 1 378 544 and EP 1 674 073.

Thus, mention may very particularly be made of the cationic direct dyes corresponding to the following formulae:

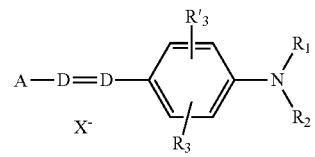

in which:
D represents a nitrogen atom or the —CH group,
$R_1$ and $R_2$, which are identical or different, represent a hydrogen atom; a $C_1$-$C_4$ alkyl radical which can be substituted by a —CN, —OH or —NH$_2$ radical or can form, with a carbon atom of the benzene ring, an optionally oxygen-comprising or nitrogen-comprising heterocycle which can be substituted by one or more $C_1$-$C_4$ alkyl radicals; or a 4'-aminophenyl radical,
$R_3$ and $R'_3$, which are identical or different, represent a hydrogen atom, a halogen atom chosen from chlorine, bromine, iodine and fluorine, a cyano radical, a $C_1$-$C_4$ alkyl radical, a $C_1$-$C_4$ alkoxy radical or an acetyloxy radical,
$X^-$ represents an anion, preferably chosen from chloride, methyl sulphate and acetate,
A represents a group chosen from the following structures:

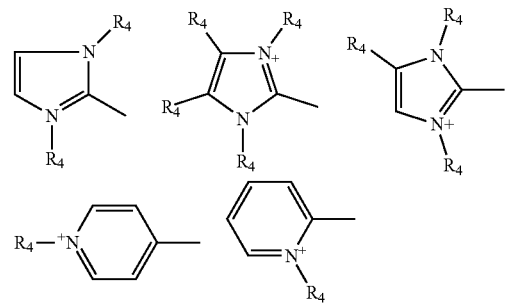

in which $R_4$ represents a $C_1$-$C_4$ alkyl radical which can be substituted by a hydroxyl radical;

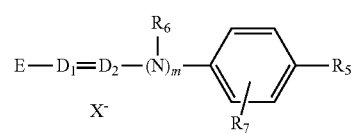

in which:
$R_5$ represents a hydrogen atom, a $C_1$-$C_4$ alkoxy radical or a halogen atom, such as bromine, chlorine, iodine or fluorine,
$R_6$ represents a hydrogen atom or a $C_1$-$C_4$ alkyl radical or forms, with a carbon atom in the benzene ring, a heterocycle which optionally comprises oxygen and/or is optionally substituted by one or more $C_1$-$C_4$ alkyl groups, $R_7$ represents a hydrogen atom or a halogen atom, such as bromine, chlorine, iodine or fluorine, $D_1$ and $D_2$, which are identical or different, represent a nitrogen atom or the —CH group, m=0 or 1, $X^-$ represents a cosmetically acceptable anion preferably chosen from chloride, methyl sulphate and acetate, E represents a group chosen from the following structures:

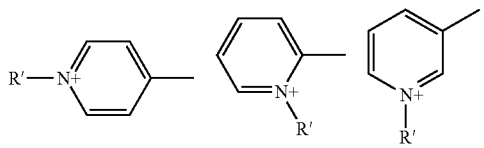

in which R' represents a $C_1$-$C_4$ alkyl radical;

when m=0 and when $D_1$ represents a nitrogen atom, then E can also denote a group with the following structure:

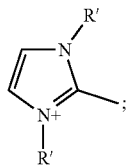

in which R' represents a $C_1$-$C_4$ alkyl radical.

The synthetic direct dye may be selected from fluorescent dyes. Two or more types of fluorescent dyes may be used in combination.

The use of some fluorescent dyes may make it possible to obtain, on dark hair, colors which are more visible than with conventional hydrophilic or hydrophobic direct dyes.

Furthermore, these fluorescent dyes, when applied to dark hair, may also make it possible to lighten the hair without damaging it.

As used herein, the term "fluorescent dyes" is understood to mean fluorescent compounds and optical brighteners. In at least one embodiment, the fluorescent dye is soluble in the medium of the composition according to the present invention.

Fluorescent dyes are fluorescent compounds which absorb visible radiation, for example, wavelengths ranging from 400 to 800 nm, and which are capable of re-emitting light in the visible region at a higher wavelength.

According to one embodiment, the fluorescent dyes useful for the present invention re-emit orange-colored fluorescent light. They exhibit, for instance, a maximum re-emission wavelength ranging from 500 to 700 nm.

Non-limiting examples of fluorescent dyes include compounds known in the art, for example, those described in Ullmann's Encyclopedia of Industrial Chemistry, Release 2004, 7th edition, "Fluorescent Dyes" chapter.

The optical brighteners of the present disclosure, also known under the name of "brighteners", or "fluorescent brighteners", or "fluorescent brightening agents" or "FWA", or "fluorescent whitening agents", or "whiteners", or "fluorescent whiteners", are colorless transparent compounds as they do not absorb visible light but only in ultraviolet light (wavelengths ranging from 200 to 400 nanometers) and convert the energy absorbed into fluorescent light of higher wavelength emitted in the visible part of the spectrum, generally in the blue and/or green, that is to say in wavelengths ranging from 400 to 550 nanometers.

Optical brighteners are known in the art, for example, they are described in Ullmann's Encyclopedia of Industrial Chemistry (2002), "Optical Brighteners" and Kirk-Othmer Encyclopedia of Chemical Technology (1995): "Fluorescent Whitening Agents".

The fluorescent dyes which can be used in the composition according to the present invention include compounds known from the art, for example, those described in French Patent No. 2 830 189.

Soluble fluorescent compounds that may especially be mentioned include those belonging to the following families: naphthalimides, coumarins, xanthenes and in particular xanthenodiquinolizines and azaxanthenes; naphtholactams; azlactones; oxazines; thiazines; dioxazines; azo compounds; azomethines; methines; pyrazines; stilbenes; ketopyrroles; and pyrenes.

If present, the fluorescent dyes are preferred, more particularly, those re-emitting orange-colored fluorescent light.

In terms of ionic nature, the direct dye may be selected from the group consisting of acidic direct dyes, basic direct dyes and neutral direct dyes, which covers all possible types of direct dyes, such as so-called nitro dyes and HC dyes. Acidic direct dyes have an anionic moiety in their chemical structure. Basic direct dyes have a cationic moiety in their chemical structure. Neutral direct dyes are nonionic.

According to an embodiment, it is preferable that the direct dye be selected from acidic direct dyes.

The anionic direct dyes are commonly known as "acidic direct dyes" for their affinity with alkaline substances (see, for example, "Industrial Dyes, Chemistry, Properties, Application", Klaus Hunger Ed. Wiley-VCH Verlag GmbH & Co KGaA, Weinheim 2003). Anionic or acid dyes are known in the literature (see, for example, "Ullman's Encyclopedia of Industrial Chemistry", Azo Dyes, 2005 Wiley-VCH Verlag GmbH & Co. KGaA, Weinheim 10.1002/14356007.a03 245, point 3.2; ibid, Textile Auxiliaries, 2002 Wiley-VCH Verlag GmbH & Co. KGaA, Weinheim 10.1002114356007.a26 227 and "Ashford's Dictionary of Industrial Chemicals", Second Edition, p. 14-p. 39, 2001). Anionic or acid dyes cause less skin irritation as compared to other direct dyes.

The term "anionic direct dyes" means any direct dye comprising in its structure at least one sulfonate group $SO_3^-$ and/or at least one carboxylate group $C(O)O^-$ and/or at least one phosphonate group $P(=O)O^-O^-$ and optionally one or more anionic groups $G^-$ with $G^-$, which may be identical or different, representing an anionic group chosen from alkoxide $O^-$, thioalkoxide $S^-$, phosphonate, carboxylate and thiocarboxylate: $C(Q)Q'^-$ with Q and Q', which may be identical or different, representing an oxygen or sulfur atom; preferably, $G^-$ represents a carboxylate, i.e. Q and Q' represent an oxygen atom.

The preferred anionic dyes of the formula of the present invention are chosen from acidic nitro direct dyes, acidic azo dyes, acidic azine dyes, acidic triarylmethane dyes, acidic indoamine dyes, acidic anthraquinone dyes, anionic styryl dyes, and indigoids and acidic natural dyes; each of these dyes containing at least one sulfonate, phosphonate or carboxylate group bearing a cationic counterion $X^+$, where $X^+$ represents an organic or mineral cationic counter ion preferably chosen from alkali and alkaline-earth metals, such as Na and $K^+$ Preferred acid dyes may be chosen from:
a) the diaryl anionic azo dyes of formula (II) or (II'):

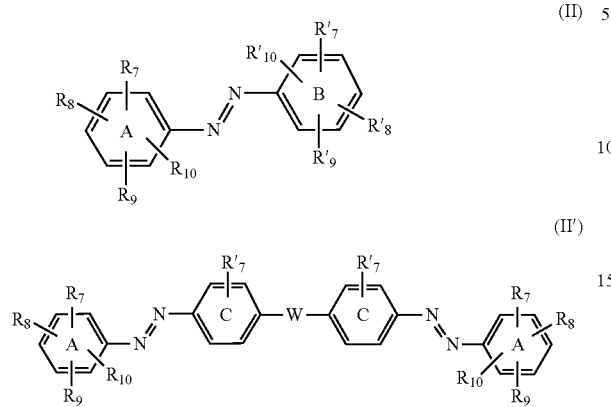

in which formulae (II) and (II'):
$R_7$, $R_8$, $R_9$, $R_{10}$, $R'_7$, $R'_8$, $R'_9$ and $R'_{10}$, which may be identical or different, represent a hydrogen atom or a group chosen from:
alkyl;
alkoxy, alkylthio;
hydroxyl, mercapto;
nitro;
R°—C(X)—X'—, R°—X'—C(X)—, R°—X'—C(X)—X"— with R° representing a hydrogen atom or an alkyl or aryl group; X, X' and X", which may be identical or different, representing an oxygen or sulfur atom, or NR with R representing a hydrogen atom or an alkyl group;
$(O)_2S(O^-)$—, $X^+$ as defined previously;
$(O)CO^-$—, $X^+$ as defined previously;
$(O)P(O_2^-)$—, $2X^+$ as defined previously;
R'''—$S(O)_2$—, with R''' representing a hydrogen atom or an alkyl, aryl,
(di)(alkyl)amino or aryl(alkyl)amino group; preferably a phenylamino or phenyl group;
R'''—$S(O)_2$—X'— with R''' representing an alkyl or optionally substituted aryl group, X' as defined previously;
(di)(alkyl)amino;
aryl(alkyl)amino optionally substituted with one or more groups chosen from i) nitro; ii) nitroso; iii) $(O)_2S(O^-)$—, $X^+$ and iv) alkoxy with $X^+$; optionally substituted heteroaryl; preferably a benzothiazolyl group;
cycloalkyl; especially cyclohexyl,
Ar—N=N— with Ar representing an optionally substituted aryl group, preferably a phenyl optionally substituted with one or more alkyl, $(O)_2S(O^-)$—, $X^+$ or phenylamino groups;
or alternatively two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more groups chosen from i) nitro; ii) nitroso; iii) $(O)_2S(O^-)$—, $X^+$; iv) hydroxyl; v) mercapto; vi) (di)(alkyl)amino; vii) R°—C(X)—X'—; viii) R°—X'—C(X)—; ix) R°—X'—C(X)—X"—; x) Ar—N=N— and xi) optionally substituted aryl(alkyl)amino; with $X^+$, R°, X, X', X" and Ar as defined previously;

W represents a sigma bond σ, an oxygen or sulfur atom, or a divalent radical i) —NR— with R as defined previously, or ii) methylene —$C(R_a)(R_b)$— with $R_a$ and $R_b$, which may be identical or different, representing a hydrogen atom or an aryl group, or alternatively $R_a$ and $R_b$ form, together with the carbon atom that bears them, a spiro cycloalkyl; preferably W represents a sulfur atom or $R_a$ and $R_b$ together form a cyclohexyl;
it being understood that formulae (II) and (II') comprise at least one sulfonate $(O)_2S(O^-)$—, $X^+$ or phosphonate $(O)P(O_2^-)$ $2X^+$ or carboxylate $(O)C(O^-)$—, $X^+$ radical on one of the rings A, A', B, B' or C with $X^+$ as defined previously;
As examples of dyes of formula (H), mention may be made of Acid Red 1, Acid Red 4, Acid Red 13, Acid Red 14, Acid Red 18, Acid Red 27, Acid Red 32, Acid Red 33, Acid Red 35, Acid Red 37, Acid Red 40, Acid Red 41, Acid Red 42, Acid Red 44, Acid Red 68, Acid Red 73, Acid Red 135, Acid Red 138, Acid Red 184, Food Red 1, Food Red 13, Food Red 17, Acid Orange 4, Acid Orange 6, Acid Orange 7, Acid Orange 10, Acid Orange 19, Acid Orange 20, Acid Orange 24, Acid Yellow 9, Acid Yellow 36, Acid Yellow 199, Food Yellow 3; Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2, Pigment Red 57; and as examples of dyes of formula (II'), mention may be made of Acid Red 111, Acid Red 134, Acid yellow 38;
b) the anthraquinone dyes of formulae (III) and (III'):

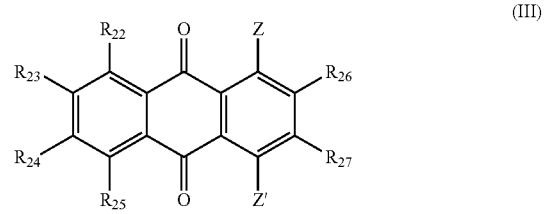

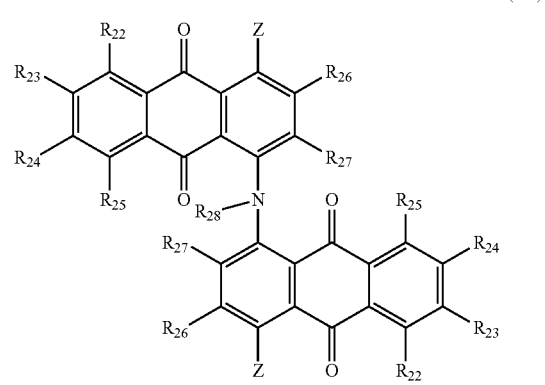

in which formulae (III) and (III'):
$R_{22}$, $R_{23}$, $R_{24}$, $R_{25}$, $R_{26}$ and $R_{27}$, which may be identical or different, represent a hydrogen or halogen atom or a group chosen from:
alkyl;
hydroxyl, mercapto;
alkoxy, alkylthio;
aryloxy or arylthio optionally substituted, preferably substituted with one or more groups chosen from alkyl and $(O)_2S(O^-)$—, $X^+$ with $X^+$ as defined previously;

aryl(alkyl)amino optionally substituted with one or more groups chosen from alkyl and $(O)_2S(O^-)$—, $X^+$ with $X^+$ as defined previously;
(di)(alkyl)amino;
(di)(hydroxyalkyl)amino;
$(O)_2S(O^-)$—, $X^+$ with $X^+$ as defined previously;

Z' represents a hydrogen atom or the group $NR_{28}R_{29}$ with $R_{28}$ and $R_{29}$, which may be identical or different, representing a hydrogen atom or a group chosen from:
alkyl;
polyhydroxyalkyl such as hydroxyethyl;
aryl optionally substituted with one or more groups, particularly i) alkyl such as methyl, n-dodecyl, n-butyl; ii) $(O)_2S(O^-)$—, $X^+$ with $X^+$ as defined previously; iii) $R°$—$C(X)$—$X'$—, $R°$—$X'$—$C(X)$—, $R°$—$X'$—$C(X)$—$X''$— with $R°$, X, X' and X'' as defined previously, preferably $R°$ represents an alkyl group;
cycloakyl; especially cyclohexyl;

Z represents a group chosen from hydroxyl and $NR'28R'29$ with $R'28$ and $R'29$, which may be identical or different, representing the same atoms or groups as $R_{28}$ and $R_{29}$ as defined previously;

it being understood that formulae (III) and (III') comprise at least one sulfonate group $(O)_2S(O^-)$—, $X^+$ with $X^+$ as defined previously;

As examples of dyes of formula (III), mention may be made of Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3; EXT Violet 2, and as examples of dyes of formula (III'), mention may be made of Acid Black 48; and g) the quinoline-based dyes of formula (IV):

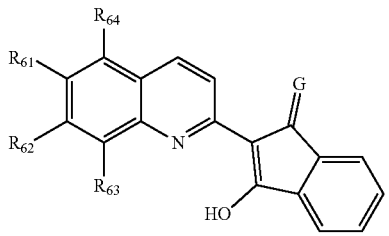

(IV)

in which formula (IV):
$R_{61}$ represents a hydrogen or halogen atom or an alkyl group;
$R_{62}$, $R_{63}$ and $R_{64}$, which may be identical or different, represent a hydrogen atom or the group $(O)_2S(O^-)$—, $X^+$ with $X^+$ as defined previously;
or alternatively $R_{61}$ with $R_{62}$, or $R_{61}$ with $R_{64}$, together form a benzo group optionally substituted with one or more of the groups $(O)_2S(O^-)$—, $X^+$ with $X^+$ as defined previously;
G represents an oxygen or sulfur atom or the group $NR_e$ with $R_e$ representing a hydrogen atom or an alkyl group; particularly G represents an oxygen atom;
it being understood that formula (IV) comprises at least one sulfonate group $(O)_2S(O^-)$—, with $X^+$ as defined previously;

As examples of the dyes of formula (IV), mention may be made of Acid Yellow 2, Acid Yellow 3 and Acid Yellow 5.

It is preferable that the acidic direct dye be selected from the group consisting of Acid Orange 4, Ext. Violet 2, Acid Yellow 5 and Acid Black 1.

The amount of the direct dye(s) in the composition according to the present invention may be 5% by weight or less, preferably 3% by weight or less, and more preferably 1% by weight or less, relative to the total weight of the composition.

The amount of the direct dye(s) in the composition according to the present invention is 0.01% by weight or more, preferably 0.03% by weight or more, and more preferably from 0.05% by weight or more, relative to the total weight of the composition.

The composition according to the present invention may contain the direct dye(s) in an amount of from 0.01% to 5% by weight, preferably from 0.03% to 3% by weight, and more preferably 0.05% to 1% by weight, relative to the total weight of the composition.

{Oil}

The composition according to the present invention comprises at least one oil. If two or more oils are used, they may be the same or different.

Here, "oil" means a fatty compound or substance which is in the form of a liquid or a paste (non-solid) at room temperature (25° C.) under atmospheric pressure (760 mmHg). As the oils, those generally used in cosmetics can be used alone or in combination thereof. These oils may be volatile or non-volatile.

The oil may be a non-polar oil such as a hydrocarbon oil, a silicone oil, or the like; a polar oil such as a plant or animal oil and an ester oil or an ether oil; or a mixture thereof.

The oil may be selected from the group consisting of oils of plant or animal origin, synthetic oils, silicone oils, hydrocarbon oils, and fatty alcohols.

As examples of plant oils, mention may be made of, for example, linseed oil, *camellia* oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate, and isostearyl neopentanoate.

Esters of $C_4$-$C_{22}$ dicarboxylic or tricarboxylic acids and of $C_1$-$C_{22}$ alcohols, and esters of monocarboxylic, dicarboxylic, or tricarboxylic acids and of non-sugar $C_4$-$C_{26}$ dihydroxy, trihydroxy, tetrahydroxy, or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides, or polysaccharides.

Examples of suitable sugars that may be mentioned include sucrose (or saccharose), glucose, galactose, ribose, fucose, maltose, fructose, mannose, arabinose, xylose, and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters, and polyesters, and mixtures thereof.

These esters may be, for example, oleates, laurates, palmitates, myristates, behenates, cocoates, stearates, linoleates, linolenates, caprates, and arachidonates, or mixtures thereof such as, especially, oleopalmitate, oleostearate, and palmitostearate mixed esters, as well as pentaerythrityl tetraethyl hexanoate.

More particularly, use is made of monoesters and diesters and especially sucrose, glucose, or methylglucose monooleates or dioleates, stearates, behenates, oleopalmitates, linoleates, linolenates, and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate), and glyceryl tri(caprate/caprylate/linolenate).

Regarding detailed explanations of silicone oils, including examples of silicone oils, refer to the section of (Silicone Oil) below.

Hydrocarbon oils may be chosen from:
linear or branched, optionally cyclic, $C_6$-$C_{16}$ lower alkanes. Examples that may be mentioned include hexane, undecane, dodecane, tridecane, and isoparaffins, for instance isohexadecane, isododecane, and isodecane; and linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term "fatty" in the fatty alcohol means the inclusion of a relatively large number of carbon atoms. Thus, alcohols which have 4 or more, preferably 6 or more, and more preferably 12 or more carbon atoms are encompassed within the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that the fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, octyldodecanol, hexyldecanol, and mixtures thereof. In one embodiment, cetyl alcohol, stearyl alcohol, octyldodecanol, hexyldecanol, or a mixture thereof (e.g., cetearyl alcohol) as well as behenyl alcohol, can be used as a saturated fatty alcohol.

According to at least one embodiment, the fatty alcohol used in the composition according to the present invention is preferably chosen from cetyl alcohol, octyldodecanol, hexyldecanol, and mixtures thereof.

It may be preferable that the oil be chosen from oils with a molecular weight below 600 g/mol.

Preferably, the oil has a low molecular weight such as below 600 g/mol, chosen among ester oils with a short hydrocarbon chain or chains ($C_1$-$C_{12}$) (e.g., isopropyl lauroyl sarcosinate, isopropyl myristate, isopropyl palmitate, isononyl isononanoate, and ethyl hexyl palmitate), hydrocarbon oils (e.g., isododecane, isohexadecane, and squalane), branched and/or unsaturated fatty alcohol ($C_{12}$-$C_{30}$) type oils such as octyldodecanol and oleyl alcohol, and ether oils such as dicaprylylether.

It is preferable that the oil be chosen from hydrocarbon oils, silicone oils, and mixtures thereof.

It is more preferable that the oil be isododecane, if the oil is non-silicone oil.

The amount of the oil(s) in the composition according to the present invention is 20% by weight or more, preferably 30% by weight or more, and more preferably 40% by weight or more, relative to the total weight of the composition.

The amount of the oil(s) in the composition according to the present invention may be 80% by weight or less, preferably 70% by weight or less, and more preferably 60% by weight or less, relative to the total weight of the composition.

The amount of the oil(s) in the composition according to the present invention may be from 20% to 80% by weight, preferably from 30% to 70% by weight, and more preferably from 40% to 60% by weight, relative to the total weight of the composition.

(Silicone Oil)

The oil in the composition according to the present invention comprises at least one silicone oil. A single type of silicone oil may be used, or two or more different types of silicone oils may be used in combination.

Here, "silicone oil" means a silicone compound or substance which is in the form of a liquid or a paste at room temperature (25° C.) under atmospheric pressure (760 mmHg). As the silicone oils, those generally used in cosmetics may be used alone or in combination thereof.

Silicones or organopolysiloxanes are defined, for instance, by Walter NOLL in "Chemistry and Technology of Silicones" (1968), Academic Press. They may be volatile or non-volatile.

Thus, the silicone oil(s) may be selected from volatile silicones, non-volatile silicones and mixtures thereof.

Thus, the silicone oil may comprise either at least one volatile silicone oil or at least one non-volatile silicone oil, or both of at least one volatile silicone oil and at least one non-volatile silicone oil.

The volatile or non-volatile silicone may be selected from linear, branched, or cyclic silicones, optionally modified with at least one organo-functional moiety or group.

For example, the silicone oil may be selected from the group consisting of polydialkylsiloxanes such as polydimethylsiloxanes (PDMS), polyalkylarylsiloxanes such as phenyltrimethicone, polydiarylsiloxanes, and organo-modified polysiloxanes comprising at least one organo-functional moiety or group chosen from poly(oxyalkylene) moieties or groups, amine or amide moieties or groups, alkoxy or alkoxyalkyl moieties or groups, hydroxyl or hydroxylated moieties or groups, acyloxy or acyloxyalkyl moieties or groups, carboxylic acid or carboxylate moieties or groups, hydroxyacylamino moieties or groups, acrylic moieties or groups, polyamine or polyamide moieties or groups, and oxazoline moieties.

If the silicone oil(s) is/are volatile, the silicone oil(s) may be chosen from those having a boiling point ranging from 60° C. to 260° C., for example:

(i) cyclic silicones such as polydialkylsiloxanes comprising from 3 to 7, for instance, from 4 to 6 silicon atoms. Non-limiting examples of such siloxanes include octamethylcyclotetrasiloxane marketed, for instance, under the trade name VOLATILE SILICONE® 7207 by UNION CARBIDE and SILBIONE® 70045 V2 by RHODIA, decamethylcyclopentasiloxane marketed under the trade name VOLATILE SILICONE® 7158 by UNION CARBIDE, and SILBIONE® 70045 V5 by RHODIA, KF-995 by SHIN ETSU, and dodecamethylcyclohexasiloxane (INCI: CYCLOHEXASILOXANE) marketed, for instance, under the trade name XIAMETER® PMX-246 and the trade name DC246 Fluid by Dow Corning, as well as mixtures thereof. Cyclomethicones that may also be used, for example, include those marketed under the references DC 244, DC 245, DC 344, DC 345, and DC 246 by DOW CORNING Cyclocopolymers of the dimethylsiloxane/methylalkylsiloxane type may also be used, such as SILICONE VOLATILE® FZ 3109 marketed by UNION CARBIDE, of formula

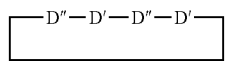

wherein:
D' is

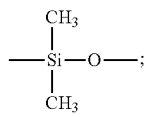

and

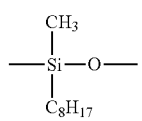

D' is

Combinations of cyclic silicones such as polydialkylsiloxanes with silicon derived organic compounds may also be used, such as an octamethylcyclotetrasiloxane and tetratrimethylsilylpentaerythritol (50/50) mixture, and an octamethylcyclotetrasiloxane and oxy-1,1'-(hexa-2,2,2',2',3,3'-trimethylsilyloxy) bis-neopentane mixture; and (ii) linear volatile polydialkylsiloxanes comprising from 2 to 9 silicon atoms. A non-limiting example of such a compound is decamethyltetrasiloxane marketed, for instance, under the trade name "SH-200" by TORAY SILICONE. Silicones belonging to this class are also described, for example, in Cosmetics and Toiletries, Vol. 91, January 1976, P. 27-32—TODD & BYERS "Volatile Silicone Fluids for Cosmetics".

If the silicone oil(s) is/are volatile, the silicone oil(s) may be chosen from cyclic silicones.

On the other hand, the silicone oil(s) may be chosen from non-volatile silicones, such as polydialkylsiloxanes, polyalkylarylsiloxanes, polydiarylsiloxanes, and organo-modified polysiloxanes as explained above.

According to one embodiment, the silicone oil(s) may be chosen from non-volatile polydialkylsiloxanes, for example, polydimethylsiloxanes with trimethylsilyl end groups known under the trade name dimethicones.

Non-limiting examples of commercial products corresponding to such polydialkylsiloxanes include:

SILBIONE® fluids of the series 47 and 70 047 and MIRASIL® fluids marketed by RHODIA, for example 70 047 fluid V 500 000;

fluids of the MIRASIL® series marketed by RHODIA;
fluids of the series 200 marketed by DOW CORNING such as DC200, with a viscosity of 60,000 mm²/s;
XIAMETER® PMX-200 SILICONE FLUID 60000CS marketed by Dow Corning;
VISCASIL® fluids of GENERAL ELECTRIC and some fluids of the SF series (e.g., SF 96 and SF 18) of GENERAL ELECTRIC; and
the fluid marketed under the reference DC 1664 by DOW CORNING Products marketed under the trade names "ABIL Wax® 9800 and 9801" by GOLDSCHMIDT belonging to this class of polydialkylsiloxanes, which are polydialkyl ($C_1$-$C_{20}$) siloxanes, may also be used.

Polyalkylarylsiloxanes may be chosen from polydimethyl/methylphenylsiloxanes, linear and/or branched polydimethyl/diphenyl siloxanes.

Non-limiting examples of such polyalkylarylsiloxanes include the products marketed under the following trade names:
SILBIONE® fluids of the 70 641 series from RHODIA;
RHODORSIL® fluids of the 70 633 and 763 series from RHODIA;
phenyltrimethicone fluid marketed under the reference DOW CORNING 556 COSMETIC GRADE FLUID by DOW CORNING;
PK series silicones from BAYER, for example, the PK20 product;
PN, PH series silicones from BAYER, for example, the PN1000 and PH1000 products; and some SF series fluids from GENERAL ELECTRIC, such as SF 1023, SF 1154, SF 1250, and SF 1265.

Organo-modified silicones which may be used according to the present invention include, but are not limited to, silicones such as those previously defined and comprising within their structure at least one organo-functional moiety or group linked directly or by means of a hydrocarbon group.

Organo-modified silicones may include, for example, polyorganosiloxanes comprising: polyethyleneoxy and/or polypropyleneoxy moieties optionally comprising $C_6$-$C_{24}$ alkyl moieties, such as products called dimethicone copolyols marketed by DOW CORNING under the trade name DC 1248 and under the trade name DC Q2-5220 and SILWET® L 722, L 7500, L 77, and L 711 fluids marketed by UNION CARBIDE, as well as PEG12 dimethicone marked under the trade name XIAMETER® OFX-0193 FLUID by DOW CORNING and ($C_{12}$)alkyl-methicone copolyol marketed by DOW CORNING under the trade name Q2 5200; optionally substituted amine moieties, for example, the products marketed under the trade name GP 4 Silicone Fluid and GP 7100 by GENESEE and the products marketed under the trade names Q2 8220 and DOW CORNING 929 and 939 by DOW CORNING Substituted amine moieties may be chosen, for example, from amino $C_1$-$C_4$ alkyl moieties. Aminosilicones or amodimethicones may have additional $C_1$-$C_4$ alkoxy functional groups, such as those corresponding to the WACKER BELSIL ADM LOG 1 product.

Aminosilicones or amodimethicones may have at least one, preferably two, additional alkyl group(s) such as $C_{12}$-$C_{20}$, preferably $C_{14}$-$C_{18}$, and more preferably $C_{16}$-$C_{18}$ alkyl groups, preferably at the terminal(s) of the molecular chain thereof, such as bis-cetearylamodimethicone, marketed under the trade name "Silsoft Ax" by Momentive Performance Materials;

alkoxylated moieties, such as the product marketed under the trade name "SILICONE COPOLYMER F-755" by SWS SILICONES and ABIL WAX® 2428, 2434, and 2440 by GOLDSCHMIDT;
hydroxylated moieties, such as hydroxyalkyl function-containing polyorganosiloxanes described, for instance, in French Patent Application No. FR-A-85 163 34;
acyloxyalkyl moieties, for example, the polyorganosiloxanes described in U.S. Pat. No. 4,957,732;
anionic moieties of the carboxylic acid type, for example, the products described in European Patent No. 0 186 507, marketed by CHISSO CORPORATION, and carboxylic alkyl anionic moieties, such as those present in the X-22-3701E product marketed by SHIN-ETSU; 2-hydroxyalkyl sulfonate; and 2-hydroxyalkyl thiosulfate such as the products marketed by GOLDSCHMIDT under the trade names <<ABIL® S201>> and <<ABIL® S255>>; hydroxyacylamino moieties, such as the polyorganosiloxanes described in European Patent Application No. 0 342 834. A non-limiting example of a corresponding commercial product is the Q2-8413 product marketed by DOW CORNING;
acrylic moieties, such as the products marketed under the names VS80 and VS70 by 3M;
polyamine moieties, and
oxazoline moieties

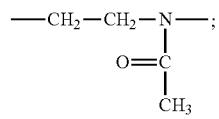

silicones that may be used according to the present invention may comprise 1 or 2 oxazoline groups; for example, poly(2-methyl oxazoline-b-dimethyl siloxane-b-2-methyl oxazoline) and poly(2-ethyl-2-oxazoline-dimethyl siloxane). The products marketed by KAO under the references OX-40, OS-51, OS-96, and OS-88 may also be used.

Polydimethylsiloxanes with dimethylsilanol end groups may also be used, for example, those sold under the trade name dimethiconol (CTFA), such as fluids of the 48 series marketed by RHODIA.

If the silicone oil(s) is/are non-volatile, the silicone oil(s) may be chosen from polydimethylsiloxanes and organo-modified polydimethylsiloxanes. The organo-modified polydimethylsiloxane may be selected from dimethicone copolyols. The viscosity of the polydimethylsiloxane or the organo-modified polydimethylsiloxane may be from 1,000,000 cst to 20,000,000 cst.

It may be preferable that the silicone oil be selected from volatile or non-volatile silicone oils, such as volatile or non-volatile polydimethylsiloxanes (PDMS) containing a linear or cyclic silicone chain, that are liquid or pasty at ambient temperature, in particular cyclopolydimethylsiloxanes (cyclomethicones) such as cyclopentasiloxane and cyclohexasiloxane; polydimethylsiloxanes containing alkyl, alkoxy, or phenyl groups that are pendent and/or at the end(s) of the silicone chain, which groups have from 1 to 24 carbon atoms; phenyl silicones such as phenyltrimethicones, phenyldimethicones, phenyltrimethylsiloxydiphenylsiloxanes, diphenyldimethicones, diphenylmethyldiphenyltrisiloxanes, 2-phenylethyltrimethyl siloxysilicates, and polymethylphenylsiloxanes; and organo-modified silicones such as dimethiconol, dimethicone copolyol (e.g., PEG12 dimethicone and PEG14 dimethicone) and amodimethicone (e.g., bis-cetearylamodimethicone).

It is possible to use a combination of at least one volatile silicone and at least one non-volatile silicone, as the silicone oil. Non-limiting examples of such combinations include a mixture of cyclopentasiloxane and dimethiconol, marketed, for instance, under the trade name Xiameter PMX-1501 Fluid by Dow Corning.

The amount of the silicone oil in the composition according to the present invention may be 1% by weight or more, preferably 3% by weight or more, and more preferably 5% by weight or more, relative to the total weight of the composition.

On the other hand, the amount of the silicone oil in the composition according to the present invention may be 25% by weight or less, preferably 20% by weight or less, and more preferably 15% by weight or less, relative to the total weight of the composition.

Accordingly, the amount of the silicone oil in the composition according to the present invention may range from 1% to 25% by weight, preferably from 3% to 20% by weight, and more preferably from 5% to 15% by weight, relative to the total weight of the composition.

{Polyol}

The composition according to the present invention may comprise at least one polyol. A single type of polyol may be used, but two or more different types of polyol may be used in combination.

The term "polyol" here means an alcohol having two or more hydroxy groups, and does not encompass a saccharide or a derivative thereof. The derivative of a saccharide includes a sugar alcohol which is obtained by reducing one or more carbonyl groups of a saccharide, as well as a saccharide or a sugar alcohol in which the hydrogen atom or atoms in one or more hydroxy groups thereof has or have been replaced with at least one substituent such as an alkyl group, a hydroxyalkyl group, an alkoxy group, an acyl group or a carbonyl group.

The polyols used in the present invention are liquid at ambient temperature such as 25° C. under atmospheric pressure (760 mmHg or 105 Pa).

The polyol may be a $C_2$-$C_{24}$ polyol, preferably a $C_2$-$C_9$ polyol, comprising at least 2 hydroxy groups, and preferably 2 to 5 hydroxy groups.

The polyol may be a natural or synthetic polyol. The polyol may have a linear, branched or cyclic molecular structure.

The polyol may be selected from glycerins and derivatives thereof, and glycols and derivatives thereof. The polyol may be selected from the group consisting of glycerin, diglycerin, polyglycerin, ethyleneglycol, diethyleneglycol, propyleneglycol, dipropyleneglycol, butyleneglycol, penty-leneglycol, hexyleneglycol, $C_6$-$C_{24}$ polyethyleneglycol, 1,3-propanediol, 1,4-butanediol, and 1,5-pentanediol.

It is preferable that the polyol be selected from the group consisting of glycerin, ethyleneglycol, polyethyleneglycol, propyleneglycol, dipropyleneglycol, butyleneglycol, penty-leneglycol, hexyleneglycol and mixtures thereof.

The amount of the polyol(s) in the composition used in the present invention may be 1% by weight or more, preferably 5% by weight or more, and more preferably 10% by weight or more, relative to the total weight of the composition.

On the other hand, the amount of the polyol(s) in the composition used in the present invention may be 30% by weight or less, preferably 25% by weight or less, and more preferably 20% by weight or less, relative to the total weight of the composition.

The amount of the polyol(s) in the composition used in the present invention may range from 1% to 30% by weight, preferably from 5% to 25% by weight, and more preferably from 10% to 20% by weight, relative to the total weight of the composition.

{Water}

The composition according to the present invention comprises water.

The amount of the water in the composition according to the present invention may be 1% by weight or more, preferably 5% by weight or more, and more preferably 10% by weight or more, relative to the total weight of the composition.

The amount of the water in the composition according to the present invention may be 40% by weight or less, preferably 35% by weight or less, and more preferably 30% by weight or less, relative to the total weight of the composition.

Thus, the amount of the water in the composition according to the present invention may range from 1% to 40% by weight, preferably from 5% to 35% by weight, and more preferably from 10% to 30% by weight, relative to the total weight of the composition.

According to the present invention, the weight ratio of the amount of the water/the amount of the polyol may be 3 or less, preferably 2 or less, more preferably 1 or less, and even more preferably 0.8 or less.

On the other hand, the weight ratio of the amount of the water/the amount of the polyol may be 0.1 or more, preferably 0.2 or more, more preferably 0.3 or more, and even more preferably 0.4 or more.

Accordingly, the weight ratio of the amount of the water/the amount of the polyol may be from 0.1 to 3, preferably from 0.2 to 2, more preferably from 0.3 to 1, and even more preferably from 0.4 to 0.8.

(Hydrophilic Acrylic Polymer)

The composition according to the present invention may comprise at least one hydrophilic acrylic polymer. If two or more hydrophilic acrylic polymers are used, they may be the same or different.

The hydrophilic acrylic polymer can function as a thickener.

According to the present invention, the term "hydrophilic acrylic polymers" means non-hydrophobic and non-amphiphilic acrylic polymers.

Said hydrophilic acrylic polymers according to the present invention are either polyacrylamidomethylpropanesulfonic acid (AMPS) acrylic polymers or acrylic acid polymers.

Among the hydrophilic acrylic polymers that may be mentioned are the following polymers.

1) Acrylic Polymers Comprising at Least One Monomer Bearing a Sulfonic Group

According to a first embodiment, the hydrophilic acrylic polymer used according to the present invention comprises at least one monomer bearing a sulfonic group.

The polymers used in accordance with the present invention are homopolymers that may be obtained from at least one ethylenically unsaturated monomer bearing a sulfonic group, which may be in free form or partially or totally neutralized form.

Preferentially, the polymers in accordance with the present invention are partially or totally neutralized with a mineral base (sodium hydroxide, potassium hydroxide or aqueous ammonia) or an organic base such as monoethanolamine, diethanolamine, triethanolamine, an aminomethylpropanediol, N-methylglucamine, basic amino acids, for instance arginine and lysine, and mixtures of these compounds. They are generally neutralized.

In the present invention, the term "neutralized" means polymers that are totally or virtually totally neutralized, i.e. at least 90% neutralized.

The polymers used in the composition of the present invention generally have a number-average molecular weight ranging from 1000 to 20 000 000 g/mol, preferably ranging from 20 000 to 5 000 000 g/mol and even more preferentially from 100 000 to 1 500 000 g/mol.

These polymers according to the present invention may be crosslinked or noncrosslinked.

The monomers bearing a sulfonic group of the polymer used in the composition of the present invention are especially chosen from vinylsulfonic acid, styrenesulfonic acid, (meth)acrylamido($C_1$-$C_{22}$)alkylsulfonic acids, N—($C_1$-$C_{22}$) alkyl(meth)acrylamido($C_1$-$C_{22}$)alkylsulfonic acids such as undecylacrylamidomethanesulfonic acid, and also partially or totally neutralized forms thereof, and mixtures thereof.

According to one preferred embodiment of the present invention, the monomers bearing a sulfonic group are chosen from (meth)acrylamido($C_1$-$C_{22}$)alkylsulfonic acids, for instance acrylamidomethanesulfonic acid, acrylamidoethanesulfonic acid, acrylamidopropanesulfonic acid, 2-acrylamido-2-methylpropanesulfonic acid, 2-methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid and 2-acrylamido-2,6-dimethyl-3-heptanesulfonic acid, and also partially or totally neutralized forms thereof, and mixtures thereof.

More particularly, 2-acrylamido-2-methylpropanesulfonic acid (AMPS), and also partially or totally neutralized forms thereof, are used.

When the polymers are crosslinked, the crosslinking agents may be chosen from the polyolefinically unsaturated compounds commonly used for crosslinking polymers obtained by free-radical polymerization.

Examples of crosslinking agents that may be mentioned include divinylbenzene, diallyl ether, dipropylene glycol diallyl ether, polyglycol diallyl ether, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allylic or vinyl ethers of polyfunctional alcohols, and also the allylic esters of phosphoric and/or vinylphosphonic acid derivatives, or mixtures of these compounds.

According to one preferred embodiment of the present invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The homopolymer of monomers bearing a sulfonic group may be crosslinked with one or more crosslinking agents.

These homopolymers are generally crosslinked and neutralized, and they may be obtained according to the preparation process comprising the following steps:

(a) the monomer such as 2-acrylamido-2-methylpropanesulfonic acid in free form is dispersed or dissolved in a solution of tert-butanol or of water and tert-butanol;
(b) the monomer solution or dispersion obtained in (a) is neutralized with one or more mineral or organic bases, preferably aqueous ammonia $NH_3$, in an amount making it possible to obtain a degree of neutralization of the sulfonic acid functions of the polymer ranging from 90% to 100%;
(c) the crosslinking monomer(s) are added to the solution or dispersion obtained in (b);
(d) a standard free-radical polymerization is performed in the presence of free-radical initiators at a temperature ranging from 10 to 150° C.; the polymer precipitates in the tert-butanol-based solution or dispersion.

The preferred AMPS homopolymers are generally characterized in that they comprise, randomly distributed:
a) from 90% to 99.9% by weight of units of general formula (II) below:

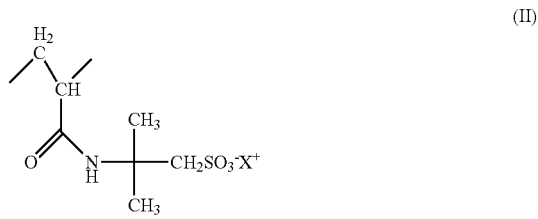

(II)

in which $X^+$ denotes a proton, an alkali metal cation, an alkaline-earth metal cation or the ammonium ion, not more than 10 mol % of the cations $X^+$ possibly being protons $H^+$;
b) from 0.01% to 10% by weight of crosslinking units derived from at least one monomer containing at least two olefinic double bonds; the weight proportions being defined relative to the total weight of the polymer.

The homopolymers according to the present invention that are more particularly preferred comprise from 98% to 99.5% by weight of units of formula (II) and from 0.2% to 2% by weight of crosslinking units.

A polymer of this type that may especially be mentioned is the crosslinked and neutralized 2-acrylamido-2-methylpropanesulfonic acid homopolymer sold by the company Clariant under the trade name Hostacerin AMPS (CTFA name: ammonium polyacryldimethyltauramide) or Simulgel 800 (CTFA name: ammonium polyacryloyldimethyl taurate) sold by the company Seppic.

As other acrylic polymers comprising at least one monomer bearing a sulfonic group, mention may especially be made of acryloyldimethyltaurate polymer, preferably acryloyldimethyltaurate copolymer. Acryloyldimethyltaurate polymer is a polymer comprising acryloyldimethyltaurate as a monomer, and acryloyldimethyltaurate copolymer is a copolymer comprising acryloyldimethyltaurate as a monomer and one or more other monomers. As the acryloyldimethyltaurate copolymer, mention may be made of a copolymer of acryloyldimethyltaurate, and vinylpyrrolidone (VP) such as ammonium acryloyldimethyl taurate/VP copolymer, sold under the name Aristoflex AVC from Clariant.

2) Acrylamide/AMPS Copolymers

According to another embodiment, the hydrophilic acrylic polymer is a crosslinked anionic copolymer formed from units derived from the reaction between (i) acrylamide (monomer 1), (ii) 2-acrylamido-2-methylpropanesulfonic acid (monomer 2, referred to hereinbelow for convenience as AMPS) and (iii) at least one polyolefinically unsaturated compound (monomer 3), constituting here the crosslinking agent.

The crosslinked anionic copolymers used in the context of the present invention are products that are already known per se and their preparation has been described especially in patent application EP-A-0 503 853, the content of which is consequently included in its entirety by reference in the present description.

The above copolymers may thus be obtained conventionally according to the emulsion polymerization technique from three different co-monomers included in their constitution.

The polyolefinically unsaturated monomers used as crosslinking agents for the preparation of the copolymers in accordance with the present invention are preferably chosen from the group formed by methylenebisacrylamide, allyl sucrose and pentaerythritol. Even more preferentially, use is made of methylenebisacrylamide.

Preferably, said polyolefinically unsaturated compound is present in the copolymer in a concentration of between 0.06 and 1 mmol per mole of the monomer units as a whole.

The ratio, expressed in mol %, between acrylamide and AMPS is preferentially between 85/15 and 15/85, advantageously between 70/30 and 30/70, even more preferentially between 65/35 and 35/65 and even more particularly between 60/40 and 40/60. In addition, AMPS is generally at least partially neutralized in the form of a salt, for example with sodium hydroxide, with potassium hydroxide or with a low molecular weight amine such as triethanolamine, or mixtures thereof.

A crosslinked copolymer that is particularly preferred in the context of the implementation of the present invention corresponds to the one prepared in Example 1 of patent application EP-A-0 503 853 mentioned above, and which is then in the form of a water-in-oil inverse emulsion. More precisely, this copolymer is formed from 60 mol % of acrylamide and 40 mol % of the sodium salt of AMPS, and it is crosslinked with methylenebisacrylamide in a proportion of 0.22 mmol per mole of the total monomer mixture. The final water-in-oil inverse emulsion preferably contains about 40% by weight of crosslinked copolymer as defined above and about 4% by weight of an ethoxylated fatty alcohol with an HLB of about 12.5.

Crosslinked copolymers that are more particularly used according to the present invention are the products sold under the names Sepigel 305 (CTFA name: polyacrylamide/$C_{13}$-14 isoparaffin/Laureth 7) or Simulgel 600 (CTFA name: acrylamide/sodium acryloyldimethyltaurate copolymer/isohexadecane/polysorbate 80) sold by the company SEPPIC, or Simulgel EG (CTFA name: sodium acrylate/sodium acryloyldimethyltaurate copolymer/isohexadecane/polysorbate 80).

3) Other Hydrophilic Acrylic Polymers

As other hydrophilic acrylic polymers that may be used according to the present invention, mention may also be made of:

homopolymers or copolymers of acrylic or methacrylic acids or salts thereof and esters thereof, such as the products sold under the names Carbopol 934, 940, 954, 981 and 980 by the company Noveon, Synthalen L® from the company 3V, sodium polymethacrylate sold under the name Darvan No. 7® by the company Vanderbilt, the products sold under the names Versicol F or Versicol K by the company Allied Colloid, Ultrahold 8 by the company Ciba Geigy and polyacrylic acids of Synthalen K type, polyacrylates and polymethacrylates such as glyceryl acrylate polymers, and in particular copolymers of glyceryl acrylate and of acrylic acid, such as the products sold under the names Lubrajel® MS, Lubrajel® CG, Lubrajel® DV, Lubrajel® NP, Lubrajel® OIL Lubrajel® Oil BG, Lubrajel® PF, Lubrajel® TW and Lubrajel® WA by the company Guardian Laboratories. Use is preferably made of Lubrajel MS, polyacrylic acid/alkyl acrylate copolymers of Pemulen type, copolymers of acrylic acid salt/vinyl alcohol, such as the product sold under the name Hydragen FN® from Cognis, and mixtures thereof.

It may be preferable that the hydrophilic acrylic polymer be selected from acrylamide/AMPS copolymers.

The amount of the hydrophilic acrylic polymer in the composition according to the present invention may be 0.01% by weight or more, preferably 0.05% by weight or more, and more preferably 0.1% by weight or more, relative to the total weight of the composition.

The amount of the hydrophilic acrylic polymer in the composition according to the present invention may be 10% by weight or less, preferably 5% by weight or less, and more preferably 1% by weight or less, relative to the total weight of the composition.

Thus, the amount of the hydrophilic acrylic polymer in the composition according to the present invention may range from 0.01% to 10% by weight, preferably from 0.05% to 5% by weight, and more preferably from 0.1% to 1% by weight, relative to the total weight of the composition.

(Other Optional Additives)

The composition according to the present invention may also comprise any other optional additive(s) usually used in the field of cosmetics, chosen, for example, from anionic, cationic, amphoteric or nonionic surfactants, anionic, cationic, amphoteric or nonionic polymers, solvents, gums, resins, hydrophilic thickening agents, hydrophobic thickening agents, dispersants, antioxidants, film-forming agents, preserving agents, fragrances, neutralizers, pH adjusting agents, antiseptics, UV-screening agents, cosmetic active agents such as vitamins, moisturizers, emollients or collagen-protecting agents, and mixtures thereof.

As the pH adjusting agent, at least one acidifying agent and/or at least one basifying agent (alkaline agent) may be used.

The acidifying agents can be, for example, mineral or organic acids, for instance hydrochloric acid, phosphoric acid, carboxylic acids, for instance tartaric acid, citric acid, and lactic acid, or sulphonic acids.

The acidifying agent may be present in an amount ranging from less than 5% by weight, preferably from 3% by weight or less, and more preferably from 1% by weight or less, relative to the total weight of the composition.

The basifying agent or alkaline agent can be, for example, any inorganic or organic basic agents which are commonly used in cosmetic products such as ammonia; alkanolamines such as mono-, di- and tri-ethanolamine, isopropanolamine; metal hydroxide such as alkaline metal hydroxide (e.g., sodium and potassium hydroxides); urea, guanidine and their derivatives; and diamines such as those described in the structure below:

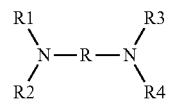

wherein
R denotes an alkylene such as propylene optionally substituted by a hydroxyl or a $C_1$-$C_4$ alkyl radical, and $R_1$, $R_2$, $R_3$, and $R_4$ independently denote a hydrogen atom, an alkyl radical, or a $C_1$-$C_4$ hydroxyalkyl radical, which may be exemplified by 1,3-propanediamine, and derivatives thereof. Alkaline metal hydroxide such as sodium hydroxide may be preferable.

The composition according to the present invention may comprise at least one water-miscible solvent such as a lower monoalcohol containing from 1 to 5 carbon atoms, $C_3$-$C_4$ ketones or $C_3$-$C_4$ aldehydes. The water-miscible solvent that can preferably be used is ethanol. The content of water-miscible solvent can range from 0.1% to 15% by weight, and better still from 1% to 8% by weight, relative to the total weight of the composition.

It is a matter of routine operations for a person skilled in the art to adjust the nature and amount of the above optional additives which may be present in the composition in accordance with the present invention such that the desired cosmetic properties are not thereby affected.

[Preparation]

The composition according to the present invention can be prepared by mixing the essential ingredient(s) as explained above, and optional ingredient(s), if necessary, as explained above.

The method and means to mix the above essential and optional ingredients are not limited. Any conventional method and means can be used to mix the above essential and optional ingredients to prepare the composition according to the present invention.

[Form]

The composition according to the present invention may be a leave-on type or rinse-off type, preferably leave-on type.

[Process]

The composition according to the present invention may preferably be used as a cosmetic composition. The cosmetic composition may be used for treating keratin fibers. The keratin fibers may be hair, eyebrows, eyelashes and the like.

In particular, the composition according to the present invention may be intended for application onto keratin fibers such as hair. Thus, the composition according to the present invention can be used for a cosmetic process for keratin fibers.

The present invention also relates to a process for keratin fibers, preferably hair, comprising the step of applying the composition according to the present invention to the keratin fibers.

The keratin fibers to which the composition according to the present invention has been applied can be left for an appropriate time which is required to treat the keratin fibers. The time length for each treatment is not limited, but it may be from 1 minute to 15 minutes, preferably from 1 minute to 10 minutes, and more preferably from 1 minute to 5 minutes. Thus, for example, the total time for the treatments according to the present invention may be from 3 to 30 minutes, preferably from 3 to 15 minutes, and more preferably from 3 minutes to 10 minutes.

The keratin fibers may be treated at room temperature. Alternatively, the keratin fibers can be heated at 15° C. to 45° C., preferably 20° C. to 40° C., more preferably 25° C. to 35° C., and even more preferably 27° C. to 35° C., before and/or during and/or after the step of applying the composition according to the present invention onto the keratin fibers.

The keratin fibers to which the composition according to the present invention has been applied may or may not be rinsed.

In one embodiment, the composition according to the present invention is applied on the wet or dry keratin fibers, preferably hair, and then dried, for example by air or a dryer.

The process, preferably cosmetic process, according to the present invention can color keratin fibers.

The process according to the present invention can be used for coloring keratin fibers, in particular for the maintenance of the color of the keratin fibers, while providing the keratin fibers with smoothness and alignment.

The process according to the present invention can be used for the maintenance of the color of the colored keratin fibers, while providing the keratin fibers with smoothness and alignment. The colored keratin fibers include the hair colored with oxidation dye or direct dye.

The process according to the present invention can also provide keratin fibers such as hair with additional improved conditioning and manageability cosmetic effects such as anti-fizz effects.

EXAMPLES

The present invention will be described in a more detailed manner by way of examples. However, these examples should not be construed as limiting the scope of the present invention.

Example 1 and Comparative Examples 1 to 5

[Preparation]

Each of the compositions for hair according to Example 1 (Ex. 1) and Comparative Examples 1 to 5 (Comp. Ex. 1 to Comp. Ex. 5) was prepared by mixing the ingredients shown in Table 1. The numerical values for the amounts of the ingredients are all based on "% by weight" as active raw materials.

TABLE 1

|  | Ex. 1 | Comp. Ex. 1 | Comp. Ex. 2 | Comp. Ex. 3 | Comp. Ex. 4 | Comp. Ex. 5 |
| --- | --- | --- | --- | --- | --- | --- |
| Ext. Violet 2 | 0.06 | 0.06 | 0.06 | 0.06 | 0.006 | 0.06 |
| Polyacrylamide (and) C13-14 Isoparaffin (and) Laureth-7 | 0.3 | 0.3 | 0.3 | 0.3 | 0.3 | 0.3 |
| Phenoxyethanol | 0.8 | 0.8 | 0.8 | 0.8 | 0.8 | 0.8 |
| PEG-14 Dimethicone | 2 | 2 | 2 | 2 | 2 | — |
| Dimethicone | 12.2 | 12.2 | 12.2 | 12.2 | 12.2 | — |
| Dipropylene Glycol | 14 | 14 | — | 14 | 14 | 14 |
| Ethanol | 5.5 | 5.5 | 5.5 | 5.5 | 5.5 | 5.5 |
| Water | 13.5 | — | 13.5 | qsp 100 | 13.5 | 13.5 |
| Glycerin | 3 | 3 | — | 3 | 3 | 3 |
| Isododecane | qsp 100 | qsp 100 | qsp 100 | 7.64 | qsp 100 | qsp 100 |
| Presence of Water | Yes | No | Yes | Yes | Yes | Yes |
| Presence of Polyol | Yes | Yes | No | Yes | Yes | Yes |

TABLE 1-continued

|  |  | Ex. 1 | Comp. Ex. 1 | Comp. Ex. 2 | Comp. Ex. 3 | Comp. Ex. 4 | Comp. Ex. 5 |
| --- | --- | --- | --- | --- | --- | --- | --- |
|  | ≥20% Oil | Yes | Yes | Yes | No | Yes | Yes |
|  | ≥0.01% Dye | Yes | Yes | Yes | Yes | No | Yes |
|  | Presence of Silicone Oil | Yes | Yes | Yes | Yes | Yes | No |
| Stability | Stability just after preparation | Good | Poor | Poor | Poor | Good | Poor |
| Surface Friction | COF (Coefficient of Friction) | Good | Good | Good | Good | Good | Poor |
| Color Uptake | ΔE | Good | Good | Good | Good | Poor | Good |
| Sensory | Smoothness of hair when dry | Good | Poor | Poor | Poor | Good | Poor |
| Evaluation | Alignment of hair when dry | Good | Poor | Poor | Poor | Good | Poor |
| Skin Staining | Stain visibility | Good | Good | Poor | Poor | Good | Poor |

[Evaluation]

(Stability)

Just after the preparation of the compositions according to Example 1 and Comparative Examples 1 to 5, the appearance of each composition was visually observed and categorized in accordance with the following criteria. The results are shown in the line labeled "Stability just after preparation" in Table 1.

Good: Stable (no separation)

Poor: Unstable (separated)

(Surface Friction)

A hair swatch (1 g, 27 cm) to which the same amount of each of the composition according to Example 1 and Comparative Examples 1 to 5 had been applied was placed on a flat-plate and fix the root side with a hair clip. The hair swatch was scanned from root to tip using the sensor (Handy Rub Tester, Type TL701 by Trinity Lab), and the friction force was measured. The measurements were performed 5 times per one hair swatch. The same operation was repeated for the other two wet hair swatches. In total, the measurements were performed for three hair swatches. The maximum force was selected from the measured data of each hair swatch. The average value of the three maximum forces was calculated and categorized in accordance with the following criteria. The results are shown in the line labeled "COF (Coefficient of Friction)" in Table 1.

Good: ≤0.1

Poor: >0.1

§ Protocol of Application

The hair swatch was shampooed before application. The composition was then applied onto the hair swatch, and the hair swatch was dried naturally at ambient conditions.

(Color Uptake)

1 g each of the compositions according to Example 1 and Comparative Examples 1 to 5 was evenly applied onto 1 g of a hair swatch. The difference in color of the hair swatch before and after the above dyeing process was evaluated by using Minolta CM-3600A. ΔE* (between the color of the undyed original hair swatch and the color of the dyed hair swatch based on CIE1976) was determined. The ΔE thus determined was categorized in accordance with the following criteria. The results are shown in the line labeled "ΔE" in Table 1.

Good: >20

Fair: 10≤ and ≤20

Poor: <10

The larger ΔE* is, the better the color uptake is.

(Sensory Evaluation)

Using natural Japanese hair swatches, the smoothness of hair when dry and alignment of hair when dry, after the application of each of the compositions according to Example 1 and Comparative Examples 1 to 5, were evaluated by 5 panelists in accordance with the following criteria.

5: significantly more

4: more

3: benchmark

2: less

1: significantly less

The average of the scores by the panelists for each sensory assessment was categorized in accordance with the following criteria. The results are shown in the lines labeled "smoothness of hair when dry" and "alignment of hair when dry" in Table 1.

Good: ≥4

Poor: <4

§ Protocol of Application

The hair swatch was shampooed before application. The composition was applied onto the hair swatch, and the hair swatch was dried naturally at ambient conditions.

(Skin Staining)

Remaining stain on the skin, after the application of each of the compositions according to Example 1 and Comparative Examples 1 to 5, were evaluated by 5 panelists in accordance with the following criteria.

3: visible

2: slightly visible

1: not visible

The average of the scores by the panelists for each assessment was categorized in accordance with the following criteria. The results are shown in the lines labeled "stain visibility" in Table 1.

Good: <2

Poor: ≥2

§ Protocol of Application

The composition (0.02 g) was applied onto on human arms, wait for 3 minutes, then washed by water for 3.0 seconds.

Table 1 shows that the composition according to Example 1 was stable without any phase separation. The composition according to Example 1 can also provide low dry combing force which results in smooth combing. Table 1 also shows that the composition according to Example 1 can provide good coloring effects. Table 1 also shows that the composition according to Example 1 can provide hair with sufficient smoothness and alignment. Table 1 also shows that the composition according to Example 1 does not result in visible skin staining after application.

The composition according to Comparative Example 1 included no water, and was unstable. The composition according to Comparative Example 1 provided a high dry combing force which results in less smooth combing. The composition according to Comparative Example 1 provided good coloring effects. The composition according to Comparative Example 1 does not result in visible skin staining after application. However, the composition according to Comparative Example 1 provided hair with poor smoothness and poor alignment.

The composition according to Comparative Example 2 included no polyol, and was unstable. The composition according to Comparative Example 2 provided a high dry combing force which results in less smooth combing. The composition according to Comparative Example 2 provided good coloring effects. However, the composition according to Comparative Example 2 provided hair with poor smoothness and poor alignment. The composition according to Comparative Example 2 result in visible skin staining after application.

The composition according to Comparative Example 3 included oils in a total amount of less than 20% by weight relative to the total weight of the composition, and was unstable. The composition according to Comparative Example 3 provided a high dry combing force which results in less smooth combing. The composition according to Comparative Example 3 provided good coloring effects. However, the composition according to Comparative Example 3 provided hair with poor smoothness and poor alignment. The composition according to Comparative Example 3 result in visible skin staining after application.

The composition according to Comparative Example 4 included a direct dye in an amount of less than 0.01% by weight relative to the total weight of the composition. The composition according to Comparative Example 4 is stable and can provide a low dry combing force which results in smooth combing. Table 1 also shows that the composition according to Comparative Example 4 can provide hair with sufficient smoothness and alignment. The composition according to Comparative Example 4 does not result in visible skin staining after application. However, the composition according to Comparative Example 4 provides only poor coloring effects.

The composition according to Comparative Example 5 included no silicone oils, and was unstable. The composition according to Comparative Example 5 provided a high dry combing force which results in less smooth combing. The composition according to Comparative Example 5 provided good coloring effects. However, the composition according to Comparative Example 5 provided hair with poor smoothness and poor alignment. The composition according to Comparative Example 5 result in visible skin staining after application.

The invention claimed is:

1. A composition for treating keratin fibers comprising:
   (a) at least one direct dye;
   (b) (i) at least one silicone oil and (ii) at least one non-silicone oil;
   (c) at least one polyol; and
   (d) water,
   wherein:
      the (a) at least one direct dye is present in an amount of at least 0.01% by weight, relative to the total weight of the composition; and
      the (b)(ii) at least one non-silicone oil is present in an amount of at least 20% by weight, relative to the total weight of the composition.

2. The composition according to claim 1, wherein the (b)(ii) at least one non-silicone oil is present in an amount ranging from 20% to 80% by weight, relative to the total weight of the composition.

3. The composition according to claim 1, wherein the (b)(i) at least one silicone oil comprises a volatile silicone oil and/or a non-volatile silicone oil.

4. The composition according to claim 3, wherein the volatile silicone oil is selected from cyclic silicones.

5. The composition according to claim 3, wherein the non-volatile silicone oil is chosen from polydimethylsiloxanes and/or organo-modified polydimethylsiloxanes.

6. The composition according to claim 5, wherein the organo-modified polydimethylsiloxanes are chosen from dimethicone copolyols.

7. The composition according to claim 1, wherein the (b)(i) at least one silicone oil is present in an amount ranging from 1% to 25% by weight, relative to the total weight of the composition.

8. The composition according to claim 1, wherein the (b)(i) at least one silicone oil is present in an amount ranging from 5% to 15% by weight, relative to the total weight of the composition.

9. The composition according to claim 1, wherein the (c) at least one polyol is chosen from glycerin, ethyleneglycol, polyethyleneglycol, propyleneglycol, dipropyleneglycol, butyleneglycol, pentyleneglycol, hexyleneglycol, or mixtures thereof.

10. The composition according to claim 1, wherein the (c) at least one polyol is present in an amount ranging from 1% to 30% by weight, relative to the total weight of the composition.

11. The composition according to claim 1, wherein the (c) at least one polyol is present in an amount ranging from 10% to 20% by weight, relative to the total weight of the composition.

12. The composition according to claim 1, wherein the (d) water is present in an amount ranging from 1% to 40% by weight, relative to the total weight of the composition.

13. The composition according to claim 1, wherein the (d) water is present in an amount ranging from 10% to 30% by weight, relative to the total weight of the composition.

14. The composition according to claim 1, wherein the weight ratio of the amount of the (d) water to the amount of the (c) at least one polyol is 3 or less.

15. The composition according to claim 1, wherein the weight ratio of the amount of the (d) water to the amount of the (c) at least one polyol ranges from 0.1 to 3.

16. The composition according to claim 1, wherein the weight ratio of the amount of the (d) water to the amount of the (c) at least one polyol ranges from 0.3 to 1.

17. The composition according to claim 1, further comprising (e) at least one hydrophilic acrylic polymer.

18. The composition according to claim 1, wherein the composition is a leave-on or rinse-off composition.

19. A cosmetic process for treating keratin fibers, comprising applying a composition to the keratin fibers, wherein the composition comprises:
   (a) at least one direct dye;
   (b) (i) at least one silicone oil and (ii) at least one non-silicone oil;
   (c) at least one polyol; and
   (d) water,
   wherein:
      the (a) at least one direct dye is present in an amount of at least 0.01% by weight, relative to the total weight of the composition; and
      the (b)(ii) at least one non-silicone oil is present in an amount of at least 20% by weight, relative to the total weight of the composition.

* * * * *